United States Patent [19]

Gambale

[11] Patent Number: 5,372,592
[45] Date of Patent: Dec. 13, 1994

[54] METHOD AND DEVICE FOR PREPARING CATHETERS PRIOR TO USE

[75] Inventor: Richard A. Gambale, Tyngsboro, Mass.

[73] Assignee: C. R. Bard, Inc., Murray Hill, N.J.

[21] Appl. No.: 902,096

[22] Filed: Jun. 22, 1992

[51] Int. Cl.[5] .......................................... A61M 25/00
[52] U.S. Cl. ................................... 604/280; 604/283; 604/165; 604/93
[58] Field of Search ..................... 604/192, 239–240, 604/263–264, 272, 280, 93, 165

[56] References Cited

U.S. PATENT DOCUMENTS

| | | | |
|---|---|---|---|
| 1,518,531 | 12/1924 | Lung | 604/240 X |
| 2,559,474 | 7/1951 | Son | 604/263 X |
| 3,626,471 | 12/1971 | Florin | 128/20 |
| 4,669,463 | 6/1987 | McConnell | 604/283 X |
| 4,721,123 | 1/1988 | Cosentino et al. | 134/57 R |
| 4,771,782 | 9/1988 | Millar | 128/637 |
| 4,787,889 | 11/1988 | Steppe et al. | 604/22 |
| 4,844,092 | 7/1989 | Rydell et al. | 128/772 |
| 4,850,358 | 7/1989 | Millar | 128/637 |
| 4,917,094 | 4/1990 | Lynch et al. | 128/657 |
| 4,932,413 | 6/1990 | Shockey et al. | 128/657 |
| 4,946,443 | 8/1990 | Hauser et al. | 604/165 |
| 4,947,864 | 8/1990 | Shockey et al. | 128/772 |
| 4,995,872 | 2/1991 | Ferrara | 605/280 |
| 5,030,227 | 7/1991 | Rosebluth et al. | 606/192 |

FOREIGN PATENT DOCUMENTS 475855  9/1953  Italy ............................. 604/240

OTHER PUBLICATIONS

Websters New World Dictionary, Third College Edition.
Sales brochure and instruction manual for ACS RX .014" and 018' Flushing tools.

Primary Examiner—C. Fred Rosenbaum
Assistant Examiner—Corrine Maglione
Attorney, Agent, or Firm—Morgan & Finnegan

[57] ABSTRACT

A flushing tool and method for safely flushing or lubricating a guidewire lumen of a catheter is provided, having a hollow elongate member dimensioned to be inserted into the guidewire lumen of a catheter; a luer fitting secured to the proximal end of the elongate member and in flow-through communication with the elongate member; and a clip, having a pair of fingers, transversely extending from the luer fitting. The distal end of the elongate member is inserted into the guidewire lumen of the catheter, while the clip is attached to several locations along the shaft of the catheter by inserting several portions the shaft of the catheter between the fingers of the clip. Alternatively, the clip may be attached to a container used to store the catheter, with the elongate member inserted through an aperture in the container and into the guidewire lumen of the catheter. An injection device containing a flushing/lubricating solution may then be connected to the luer fitting, so that the flushing/lubricating solution can be injected through the flushing tool and the guidewire lumen.

14 Claims, 3 Drawing Sheets

FIG. I

METHOD AND DEVICE FOR PREPARING CATHETERS PRIOR TO USE

FIELD OF THE INVENTION

This invention relates generally to an apparatus and method for simplifying the preparation of percutaneous catheters, and more particularly to a tool for flushing the guidewire lumen of a monorail style coronary catheter.

BACKGROUND OF THE INVENTION

In the past few years, there has been a significant increase in the number of diagnostic and therapeutic procedures using monorail-type catheters. Monorail-type catheters, such as those disclosed in U.S. Pat. No. 4,762,129 issued to Bonzel, are used in angioplasty operations for dilating a region of stenosis in the coronary arteries. Before any angioplasty operation commences, it is typical for a physician to prepare the catheter after it is removed from its package and prior to its use.

Preparation of a monorail catheter prior to use usually involves flushing the guidewire lumen with a saline solution to improve the lubricity of the lumen, and therefore the tractability of a catheter over an in-situ guidewire. This flushing procedure also serves to cleanse the guidewire lumen of any contaminants introduced during the manufacture and packaging of the catheter.

Monorail catheters, unlike common over-the-wire catheters, are not manufactured with an integral luer fitting on the proximal end of the guidewire lumen and are usually packaged with a solid stylet inserted in the guidewire lumen to maintain its patency during shipping and storage. To prepare the catheter, the physician will typically remove the solid stylet that is inserted in the guidewire lumen and then insert the tip of a hypodermic needle of a syringe filled with fluid, into the proximal or distal end of the guidewire lumen. Care and time are required to prevent perforating the inflation lumen of the catheter during the insertion process. Once the hypodermic needle is positioned inside the guidewire lumen, the physician then flushes the appropriate cleaning/lubricating fluid through the guidewire lumen.

A major difficulty with this time consuming practice is the cumbersome handling of the typically flimsy catheter while performing the lumen flushing procedure. Moreover, accidental puncturing of the inflation lumen occurs oftentimes when the physician attempts to insert the tip of the hypodermic needle into the adjacent guidewire lumen during the flushing operation. Once such damage occurs, the catheter is unusable because it is unsafe, and must be discarded. Unfortunately, coronary catheters are quite expensive, costing several hundreds of dollars each. The cost of catheters represents a significant portion of the overall cost of the angioplasty procedure, and avoiding unnecessary damage to the catheter would be a great help in controlling the spiraling cost of medical procedures utilizing catheters.

Thus, there is a need for a device and method which facilitates the preparation and safe flushing of the guidewire lumen of a catheter while preventing accidental damage to the catheter.

Accordingly, it is an object of the present invention to provide a surgical tool for facilitating the handling of a catheter during its preparation for use.

It is another object of the present invention to provide a surgical tool that facilitates the safe flushing or lubricating of a catheter lumen while preventing accidental damage that may be caused by a misplaced hypodermic needle.

It is yet another object of the invention to provide a tool which will maintain the catheter shaft substantially stationary while its being flushed.

It is still another object to provide a catheter flushing tool that is simple in design and use, and economical to manufacture.

The foregoing objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

In accordance with these and other objects of the present invention, a brief summary of an exemplary embodiment is presented. Some simplifications and omissions may be made in the following summary, which is intended to highlight and introduce some aspects of the present invention, but not to limit its scope. Detailed descriptions of an exemplary embodiment adequate to allow those of ordinary skill in the art to make and use the inventive concepts will be provided later.

According to a broad aspect of the invention, a flushing tool for safely flushing or lubricating a guidewire lumen of a catheter is provided, having an elongate member dimensioned to be inserted into the guidewire lumen of a catheter, the elongate member including a distal end and a proximal end, and a lumen therethrough; a luer fitting secured to the proximal end of the elongate member, the luer fitting having a central lumen in communication with the lumen of the elongate member; and a clip having, for example, a pair of fingers extending from the body of the luer fitting for attaching the flushing tool to the shaft of the catheter, thereby facilitating its handling during the flushing or lubricating procedure.

The present invention also contemplates a method of preparing a catheter for use by safely flushing or lubricating the guidewire lumen using the present invention, the method broadly comprising the steps of inserting the distal end of the elongate member into the guidewire lumen of the catheter; attaching the clip to a storage hoop containing the catheter, or to the shaft of the catheter itself by inserting the shaft of the catheter between the fingers of the clip; connecting an injection device containing a flushing/lubricating solution to the luer fitting, and injecting the flushing/lubricating solution through the flushing tool and the guidewire lumen.

It is anticipated that the flushing tool would be pre-assembled and packaged with a catheter, such that the tip of the elongate member is positioned in the guidewire lumen of the catheter and the clip is coupled to several locations of the catheter shaft or, alternatively, coupled to a shipping hoop or storage container that the catheter may be stored in.

With the flushing tool and catheter assembled together, the elongate member will maintain the patency of the guidewire lumen during shipping and storage of the catheter. Additionally, handling the catheter by the clip will facilitate the flushing and lubricating preparation of the catheter. To flush the catheter, the physician simply removes the pre-assembled catheter and flushing tool from its package, connects a syringe to the luer fitting and flushes the guidewire lumen with a saline solution. The pre-assembled arrangement prevents accidental puncturing of the catheter shaft while making the flushing operation more convenient.

DETAILED DESCRIPTION OF A PREFERRED EMBODIMENT

The present invention contemplates an improved tool that facilitates the handling and flushing or lubricating of the guidewire lumen of a catheter prior to its use in an angioplasty procedure.

Figure 1:
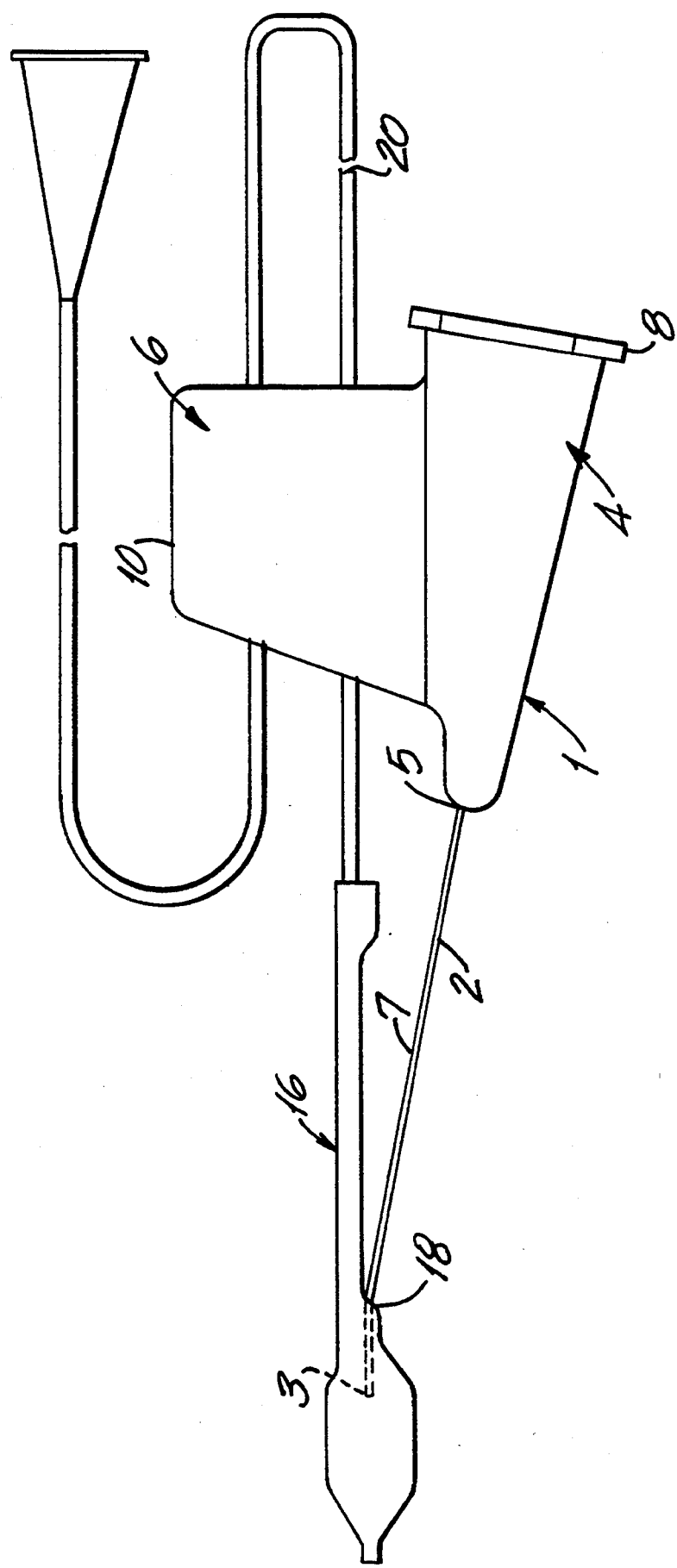
FIG. 1 is a side elevation view of a catheter flushing tool illustrating one embodiment of the present invention.
Figure 2:
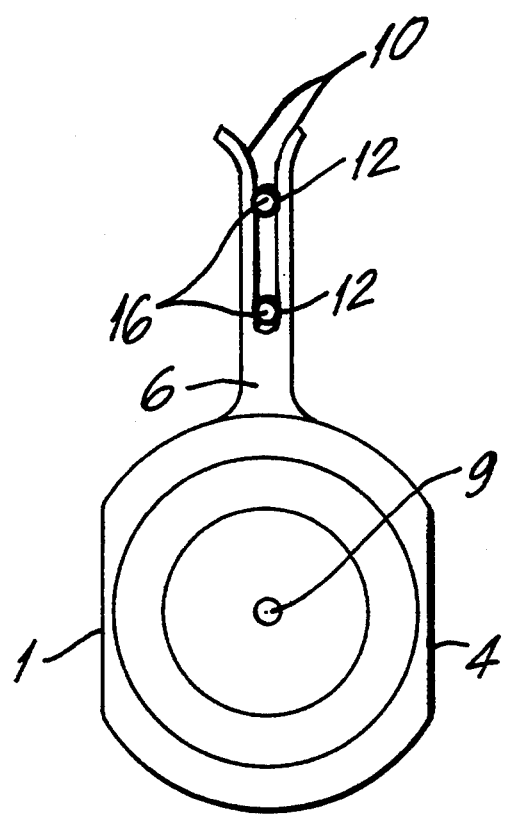
FIG. 2 is a proximal view of one end of a catheter flushing tool illustrating one embodiment of the present invention.

Referring to the drawings, there is illustrated in FIGS. 1 and 2 one embodiment of the present invention. In FIGS. 1 and 2, a catheter flushing tool X according to one embodiment of the present invention is shown.

The flushing tool 1 includes a rigid, elongated member 2 such as a hypodermic needle, having distal and proximal extremities 3 and 5, respectively, and which has a lumen 7 extending therethrough. In a preferred embodiment, the elongated member 2 has a diameter of about 0.014 inches, and may be formed of steel or a suitable biaxially orientated thermo-plastic material, such as polyimide or polyethylene terephthalate, which is commonly known by the acronym PET.

The elongate member 2 is connected at its proximal end 5 to a female luer fitting 4, having a lumen 9. The elongate member 2 and the luer fitting 4 are connected such that the lumen 7 and the lumen 9 are in flow-through communication. The luer fitting 4 contains an adapter e on the end that is not connected to the elongate member 2. The adapter 8 is designed to receive the injection port of a syringe (not shown) or the like so that a flushing/lubricating solution, such as a saline solution, may be injected through the luer fitting 4 and the elongate member 2. Accordingly, the luer fitting 4/adapter 8 may be embodied in a female configuration, or alternatively, in a male configuration. The luer fitting 4 may be formed of steel or of any of several well-known suitable thermo-plastic materials.

A clip 6 is provided for engaging the body of a catheter 16 in several locations along its length to facilitate its handling during a flushing operation. It is to be understood that the invention may be used with equal facility and advantage with various tubular medical instruments, and that the following description of a catheter, related to but not forming part of the invention, is provided for illustrative purposes only. Accordingly, the use of the catheter 16, which contains a guidewire lumen 18 and an inflation lumen 20, refers to one and not all applications of the invention.

As illustrated in FIGS. 1 and 2, the clip 6 extends transversely from the outer surface of the luer fitting 4 and has a height and width sufficient to maintain the coiled catheter 16 firmly and without substantial movement with respect to the flushing tool 1. It is preferable that the clip 6 be integrally formed with the luer fitting 4, such that the clip 6 is an extension of the luer fitting 4. However, it should be noted that the clip 6 may be formed as a separate element in which one of its extremities is removably attached to the luer fitting 4, or is bonded to the outer surface of the luer fitting 4 by the use of an adhesive, bonding agent, or the like.

The clip 6 includes a pair of slightly flexible, spaced apart fingers 10 extending from its body. The fingers 10 define an elongated passage for receiving several body portions of a catheter 16 therethrough. Optionally, the fingers 10 may include a plurality of concave indentations 12 on their inner surfaces for seating and resiliently gripping the catheter body portions placed within the clip 6, thereby facilitating a physicians handling of a naturally flimsy catheter 16. The clip 6 is preferably made from the same material as the luer fitting 4, but is not so limited.

As illustrated in FIG. 1, the clip 6 extends from the tapering body of the luer fitting 4 such that the luer fitting 4 and the elongate member 2 extending therefrom are positioned at a slight angle relative to the guidewire lumen 18 when the clip 6 is attached to the catheter body 16. The angle is preferably in the range of about 5°–15°, but is not limited to any specific degree. The flushing tool 1 is configured as such so that when it is properly clipped to several portions of a coiled catheter body 16, the distal portion 3 of the elongate member 2 fits within and supports the walls of the guidewire lumen 18 of the catheter 16 helping the maintain lumen patency during the packaging and storage of the catheter 16.

This configuration also prevents accidental piercing of or damage to the inflation lumen 20 of the catheter 16 in the event that the flushing tool 1 is unintentionally advanced. Moreover, the angled configuration of the flushing tool 1 with respect to the catheter body 16 allows the syringe (not shown) to be connected to the luer fitting 4 without interference from the catheter body 16. Advantageously, clipping or attaching the flushing tool 1 to the body of a coiled catheter 16 prevents migration of the needle out of the guidewire lumen 18, thereby facilitating the physician's handling of the catheter 16 during its preparation.

Figure 3:
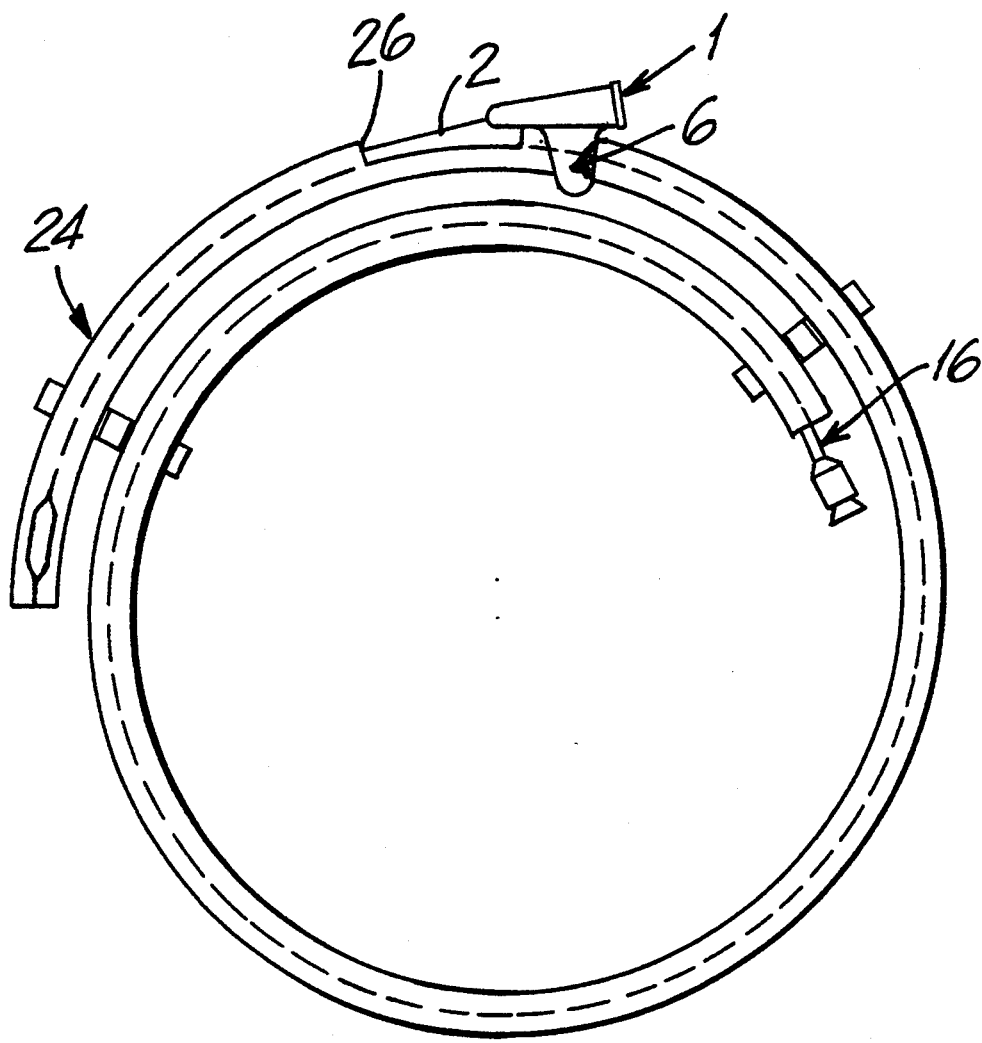
FIG. 3 is a top view of a catheter flushing tool assembled with a catheter and shipping hoop.

In an alternative arrangement, the fingers 10 may be dimensioned to received a container, such as a hoop in which the catheter may be stored during shipping and storage. As shown in FIG. 3, a shipping hoop 24 having a slot 26 in its distal area, and a catheter 16 therein is shown assembled to one embodiment of the flushing tool 1. The catheter 16 is stored within shipping hoop 24, with the balloon of the catheter 16 extending just past the distal opening of the shipping hoop 24. The clip 6 of the flushing tool 1 has the shipping hoop 24 received between the fingers 10 to prevent movement of the flushing tool 1 with respect to the shipping hoop 24. The elongate member 2 is inserted through the slot 26 and into the guidewire lumen be, as in the first embodiment described above.

It is anticipated that a catheter 16 would be pre-assembled with the flushing tool 1, such that the elongate member 2 is already inserted in the proximal end of the guidewire lumen 18 of the catheter 16, and the clip 6 is resiliently holding the shipping hoop 24, or alternatively, several portions of the body of the catheter 16 between its fingers 10. Packaging of the flushing tool 1 and the catheter 16 as an integral assembly helps maintain the patency of the guidewire lumen be during shipping and storage.

In addition to taking the place of the stylet to maintain lumen patency, the flushing tool 1 greatly facilitates the flushing operation of the guidewire lumen be once the catheter/flushing tool assembly is removed from its package. With the present invention in place, the physician simply connects a male luer fitting of a syringe (not shown) containing a flushing/lubricating solution to the adaptor e of the luer fitting 4, and injects the solution to flush any containments through the distal end of the guidewire lumen 18.

Flushing the guidewire lumen 18 also serves to lubricate the inner surfaces of the guidewire lumen 18, and thereby facilitate the tracking of the catheter 16 along an in-situ guidewire (not shown). During the entire flushing operation, the handling of the catheter 16 is facilitated by the clip 16 that is attached to several coils of the catheter 16, or alternatively, to the shipping hoop.

When the flushing operation is completed, the clip 16 is detached from the shipping hoop 24 or from the catheter body 16, whichever the case may be, and the elongate member 2 is removed from the guidewire lumen 18 of the catheter 16. The catheter 16 is now ready for use, after a simple and quick flushing operation.

It is important to note that the present invention may be used with equal facility and advantage with other catheter devices such as, e.g., conventional over-the-wire catheters. Moreover, although the invention has been described in detail with particular reference to a preferred embodiment thereof, it should be understood that the invention is capable of other and different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed:

1. A method of preparing a catheter having a guidewire lumen by safely flushing or lubricating the guidewire lumen using a device having an elongate member including a distal end and a proximal end, and a lumen therethrough; a luer member secured to said proximal end of said elongate member, said luer member having a central lumen in communication with said lumen of said elongate member; and a clip member having a pair of fingers, and extending transversely from the body of said luer member for facilitating the handling of the catheter; the method comprising the steps of:

inserting said distal end of said elongate member into the guidewire lumen of the catheter;
    attaching said clip to the body of the catheter by inserting the catheter between said fingers of said clip;
    sealingly connecting an injection device containing a flushing solution to said luer member; and
    injecting said flushing solution through said flushing device and the guidewire lumen of the catheter.

2. The method of claim 1 further comprising the step of inserting a plurality of portions of the catheter between said fingers of said clip to further facilitate the handling of the catheter.

3. The method of claim 1 further comprising the step of detaching and removing said flushing device from the catheter after flushing or lubricating the guidewire lumen.

4. A method according to claim 1, wherein said clip member, said luer member and said elongate member are configured such that said elongate member is disposed at an angle relative to said guidewire lumen when said clip member is attached to the body of the catheter.

5. A method of preparing a monorail catheter, while stored in a container having an aperture, by safely flushing or lubricating the guidewire lumen of the catheter using a device having an elongate member including a distal end and a proximal end, and a lumen therethrough; a luer member secured to said proximal end of said elongate member, said luer member having a central lumen in communication with said lumen of said elongate member; and a clip member having a pair of fingers, and extending transversely from said luer member for facilitating the handling of said catheter; the method comprising the steps of:

providing said catheter with said distal end of said elongate member inserted through the aperture in said container and into said guidewire lumen of said catheter, and said clip attached to said container, wherein said container is inserted between said fingers of said clip;
    sealingly connecting an injection device containing a flushing or lubricating solution to said luer member; and
    injecting said flushing or lubricating solution through said flushing device and said guidewire lumen, thereby cleansing and lubricating said guidewire lumen.

6. A method according to claim 5, wherein said clip member, said luer member and said elongate member are arranged such that said elongate member is disposed within the guidewire lumen, and at an angle relative to the guidewire lumen of the catheter when said clip member is coupled to the container storing the catheter, for allowing the connection of an injection device without interference from the container or the catheter.

7. A catheter assembly comprising
    a catheter member having an elongated shaft having a proximal end and a distal end and a guidewire lumen disposed in the distal end of the shaft, said guidewire lumen including a distal port and a proximal port by which the guidewire lumen communicates with the exterior of the catheter shaft;
    an elongated member having a distal end and a proximal end, and a lumen therethrough;
    an elongated flushing member having proximal and distal ends and a lumen extending between the ends of the flushing member, the distal end of said flushing member being disposed in said guidewire lumen;
    a fitting member engaged with the proximal end of said flushing member and having a lumen communicating with said flushing member lumen, said fitting including an adapter for receiving a source of flushing fluid; and
    a clip member attached to said fitting member and engaging at least one portion of said catheter for maintaining the distal end of said flushing member in said guidewire lumen of the catheter.

8. A catheter assembly as recited in claim 7 wherein said flushing member is disposed at an angle relative to the catheter.

9. A catheter assembly as recited in claim 8 wherein said angle is in the range of about 5°–15°.

10. An assembly as recited in claim 7 wherein said clip member engages said catheter in a plurality of locations.

11. A catheter assembly comprising a balloon storage member having a proximal end and a distal end and a slot disposed at the distal end thereof;

a catheter member disposed in said storage member, said catheter member having; an elongated shaft having a proximal end and a distal end and a guidewire lumen disposed in the distal end of the shaft, said guidewire lumen including a distal port and a proximal port by which the guidewire lumen communicates with the exterior of the catheter and the slot of said storage member;

an elongated flushing member having proximal and distal ends and a lumen extending between said flushing member proximal and distal ends, the distal end of said flushing member being disposed through said storage member slot and into said guidewire lumen;

a fitting member engaged with the proximal end of said flushing member and having a lumen communicating with said flushing member lumen, said fitting including an adapter for receiving a source of flushing fluid; and a clip member attached to said fitting member and engaging at least one portion of said storage member for maintaining the distal end of said flushing member in the guidewire lumen of said catheter.

12. An assembly as in claim 11 wherein said flushing member is disposed at an angle relative to the distal end of the catheter.

13. An assembly as in claim 12 wherein said angle is in the range of about 5°–15°.

14. An assembly as in claim 13 wherein said storage member is coiled in configuration and wherein said clip member engages said storage member in a plurality of locations.

* * * * *